US011344443B2

(12) United States Patent
Froula

(10) Patent No.: US 11,344,443 B2
(45) Date of Patent: May 31, 2022

(54) POSTURE SUPPORT DEVICE AND METHOD FOR SUPPORTING POSTURE

(71) Applicant: Kara Froula, Los Angeles, CA (US)

(72) Inventor: Kara Froula, Los Angeles, CA (US)

( * ) Notice: Subject to any disclaimer, the term of this patent is extended or adjusted under 35 U.S.C. 154(b) by 566 days.

(21) Appl. No.: 15/976,329

(22) Filed: May 10, 2018

(65) Prior Publication Data

US 2018/0325714 A1    Nov. 15, 2018

Related U.S. Application Data

(60) Provisional application No. 62/504,285, filed on May 10, 2017.

(51) Int. Cl.
*A61F 5/02* (2006.01)

(52) U.S. Cl.
CPC ...... *A61F 5/026* (2013.01); *A61H 2201/0192* (2013.01); *A61H 2201/1626* (2013.01); *A61H 2201/1652* (2013.01)

(58) Field of Classification Search
CPC .. A61F 5/02; A61F 5/022; A61F 5/024; A61F 5/026; A61F 5/058; A61F 5/05808; A61F 5/028; A61F 13/146; A61H 2201/1623; A41D 13/0512; A41D 13/0531; A41D 13/0007; A41D 13/0566; A41D 13/0568; A62B 35/00; A62B 35/0006; A62B 35/0012; A45F 3/047; A45F 3/04; A45F 3/10; A45F 2003/045
USPC ............................. 602/19; 128/845; 2/44, 45
See application file for complete search history.

(56) References Cited

U.S. PATENT DOCUMENTS

| 3,008,468 | A  |   | 11/1961 | Williams |
| 3,141,456 | A  |   | 7/1964  | Meek |
| 3,718,137 | A  |   | 2/1973  | Gaylord, Jr. |
| 5,662,512 | A  |   | 9/1997  | Cohen |
| 5,672,149 | A  |   | 9/1997  | Grundei |
| 6,315,747 | B1 |   | 11/2001 | Toole |
| 6,387,067 | B1 | * | 5/2002  | Hebert ............ A61F 5/026 2/44 |
| 7,568,966 | B2 |   | 8/2009  | Abbey et al. |
| 7,914,473 | B2 |   | 3/2011  | Josey |
| 8,047,893 | B2 |   | 11/2011 | Fenske |
| 8,808,212 | B1 |   | 8/2014  | Redmond |
| 10,413,438 | B1 | * | 9/2019  | Vangeloff ........... A61F 5/30 |

(Continued)

*Primary Examiner* — Alireza Nia
*Assistant Examiner* — Robin Han
(74) *Attorney, Agent, or Firm* — Michele V. Frank; Venable LLP

(57) ABSTRACT

A posture support device includes an elongate strap having: a first end comprising a first fastening member; a second end comprising a second fastening member; a first surface extending from the first end to the second end; a second surface extending from the first end to the second end; a first edge extending from the first end to the second end along a first side of the first surface and the second surface; and a second edge extending from the first end to the second end along a second side of the first surface and the second surface, the second side being opposite the first side. The strap comprises at least three pathways formed therein. In an assembled configuration, the elongate strap has a portion of the elongate strap disposed within each of the pathways and has the first and second fastening members secured to form the posture support device.

24 Claims, 21 Drawing Sheets

(56) References Cited

U.S. PATENT DOCUMENTS

2004/0235581 A1 11/2004 Citron et al.
2014/0135674 A1 5/2014 Kirk
2015/0105710 A1\* 4/2015 Constain ................ A61F 5/026
602/19

\* cited by examiner

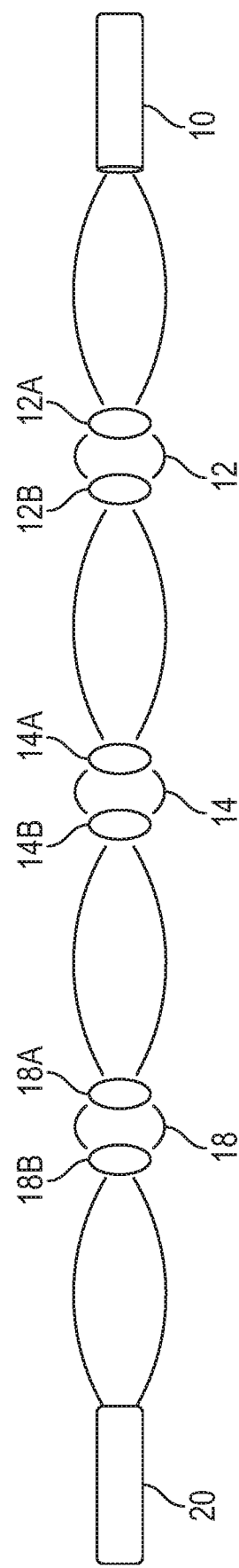

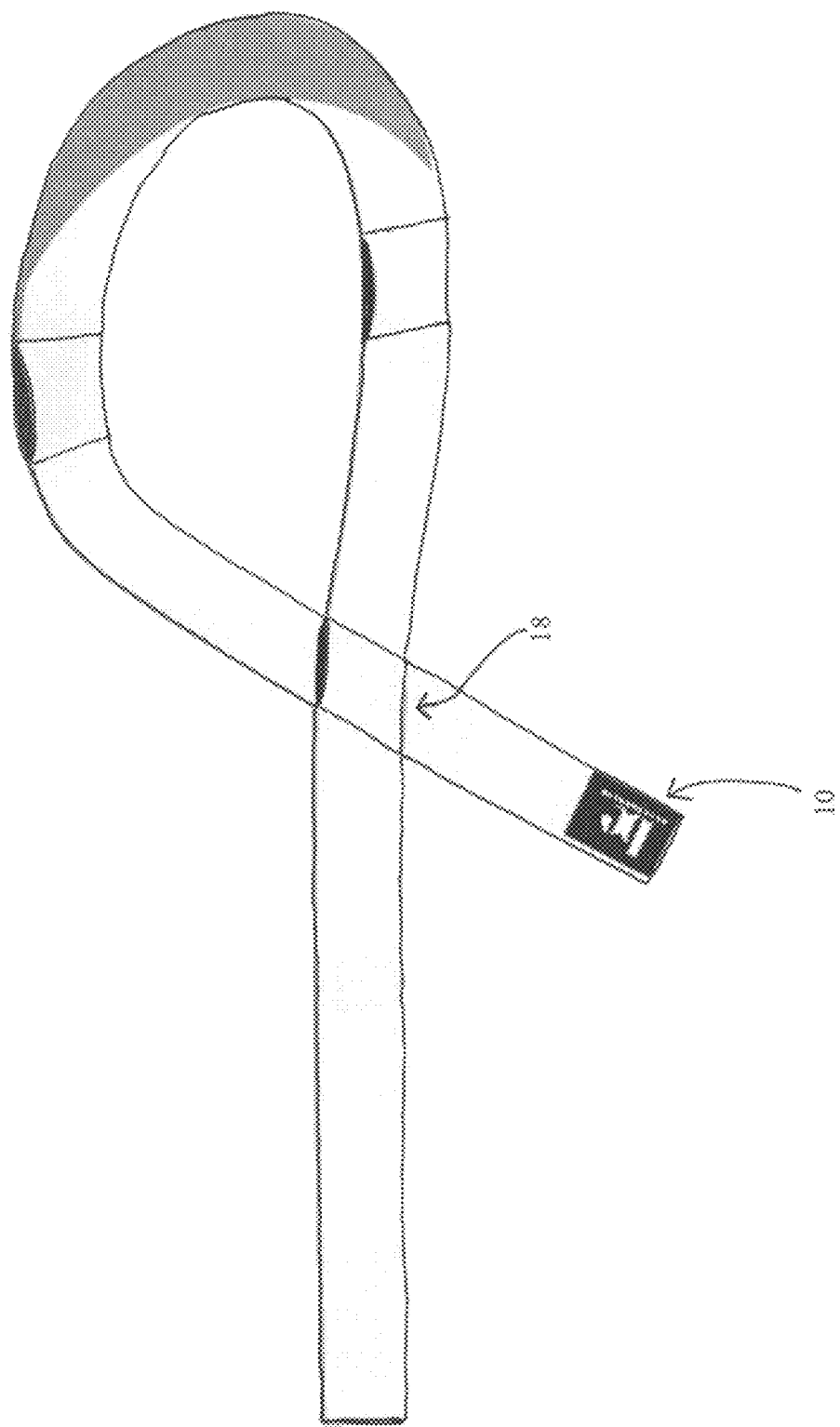

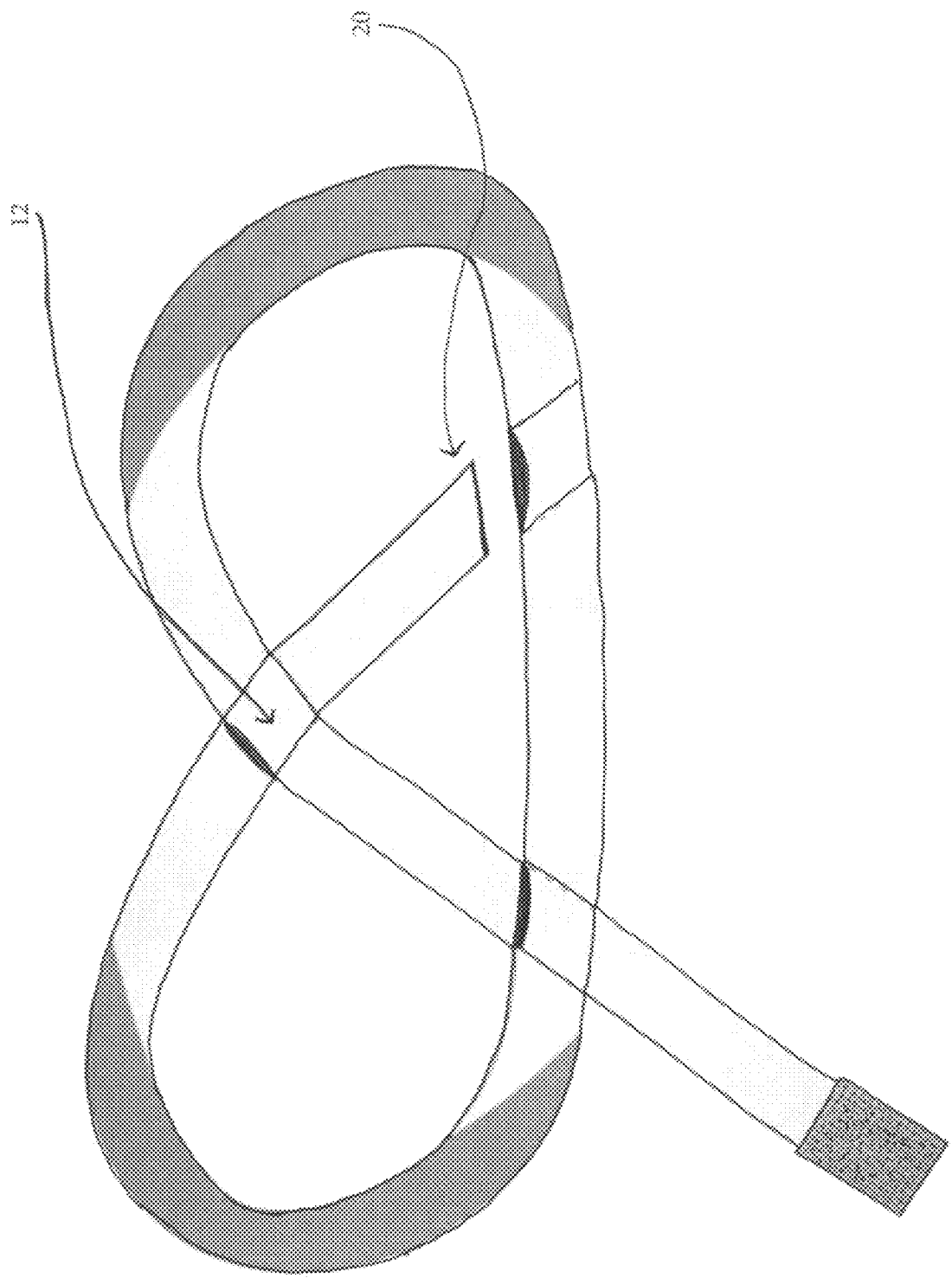

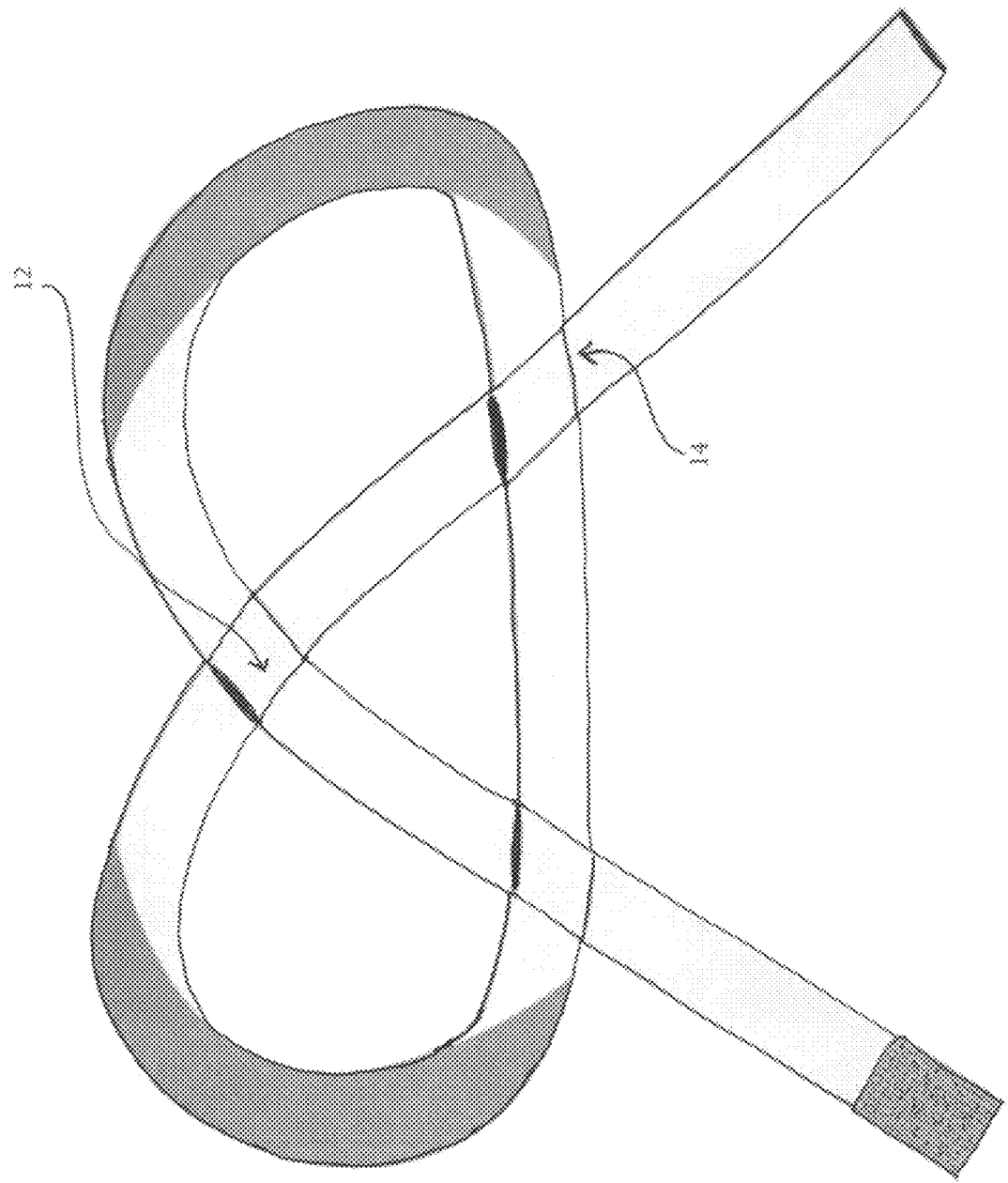

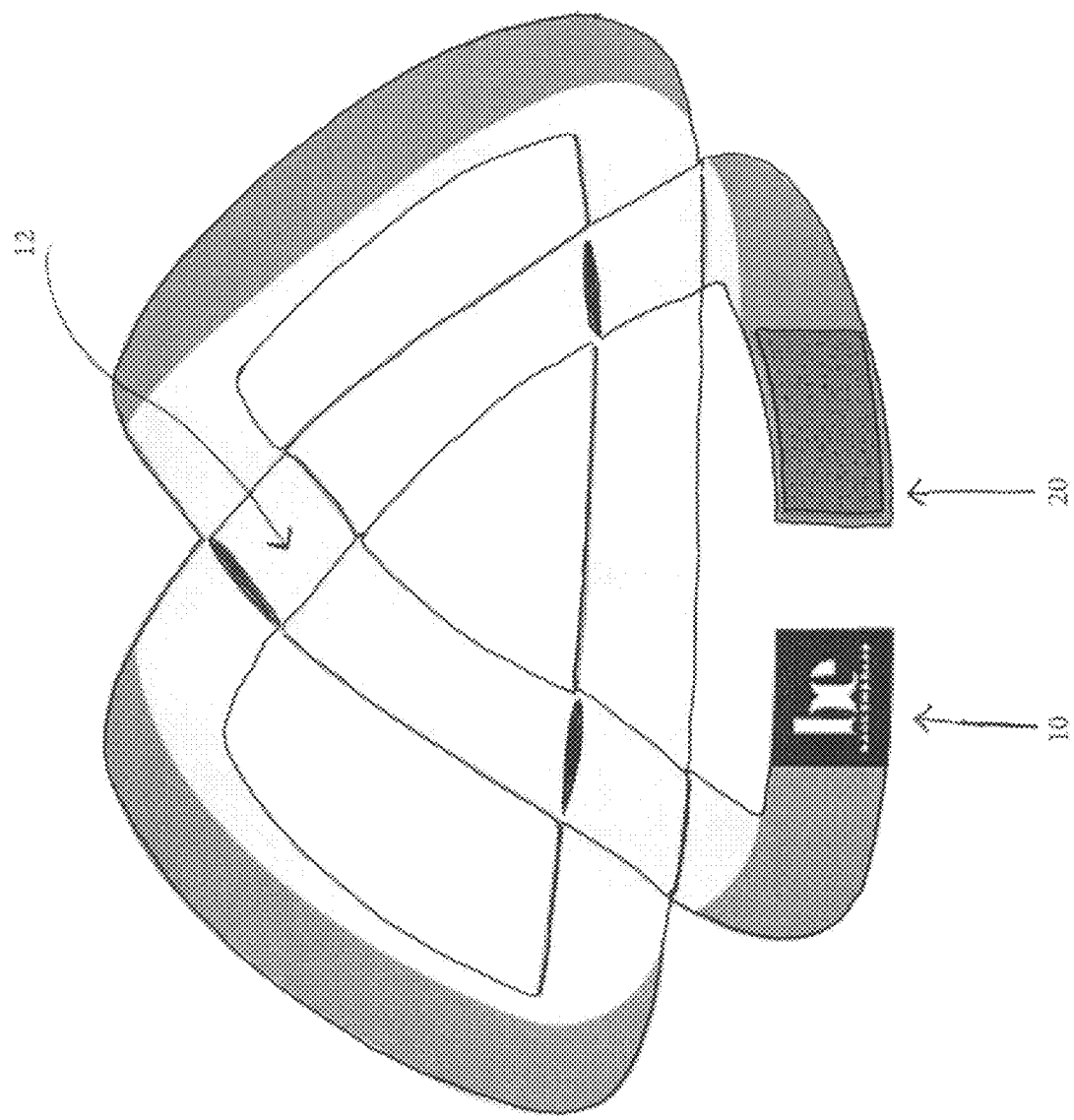

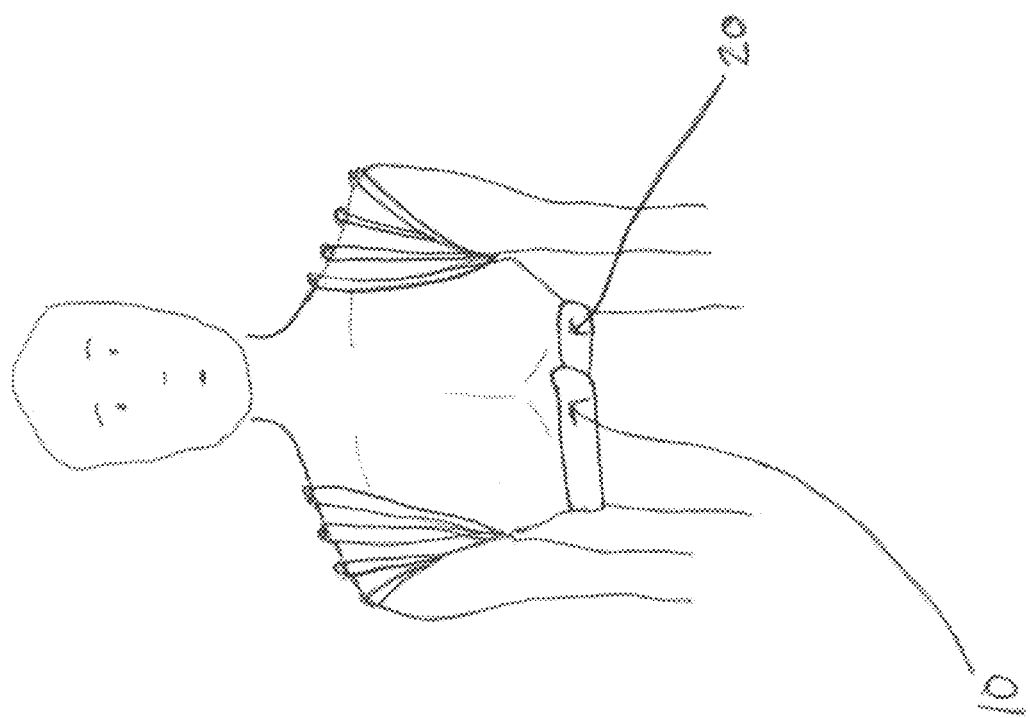

POSTURE SUPPORT DEVICE AND METHOD FOR SUPPORTING POSTURE

This application claims priority to U.S. Provisional Application No. 62/504,285 filed May 10, 2017, the entire content of which is hereby incorporated by reference.

BACKGROUND

1. Technical Field

The invention is generally directed to a self-adjusting, easy-to-wear posture support device worn over or under clothing. In one aspect, the invention uses straps to gently retract a person's shoulders to aid in proper postural alignment.

2. Discussion of Related Art

The prior art consists of other posture support devices with different structural designs which have shortcomings including skin irritation, restricted mobility, localized discomfort, bulky construction, and unattractive design. The prior art tends to focus on applying pressure around the shoulder area either in a vertically linear fashion along the spine or in other unnatural configurations, resulting in an unnatural and uncomfortable posture. One of the main flaws of the configurations seen in prior art is a lack of conformity with the upper body's anatomy and shape; hindering shoulder and arm mobility and making other body parts more susceptible to further postural dysfunctions.

SUMMARY

A posture support device according to one aspect of the invention includes an elongate strap having: a first end comprising a first fastening member; a second end comprising a second fastening member; a first surface extending from the first end to the second end; a second surface extending from the first end to the second end; a first edge extending from the first end to the second end along a first side of the first surface and the second surface; and a second edge extending from the first end to the second end along a second side of the first surface and the second surface, the second side being opposite the first side. The elongate strap comprises at least three pathways formed therein, each pathway extending from the first edge to the second edge between the first surface and the second surface. In an assembled configuration, the elongate strap is configured to have a portion of the elongate strap disposed within each of the at least three pathways and to have the first and second fastening members secured to form the posture support device.

According to one aspect, a first pathway of the at least three pathways extends perpendicular to the first edge and the second edge. According to one aspect, a second pathway and a third pathway of the at least three pathways do not extend perpendicular to the first edge and the second edge. According to one aspect, each of the at least three pathways has a width that is between 100% and 150% the width of the elongate strap.

According to one aspect, in an assembled configuration, an angle of the portion of the elongate strap disposed within each of the at least three pathways is determined by an angle of the respective pathway. According to one aspect, the elongate strap is two parallel straps, wherein the at least three pathways are formed between opposing inner surfaces of the two parallel straps. According to one aspect, the two parallel straps are joined only at the first end, the second end, and on either side of each of the three pathways. According to one aspect, wherein the two parallel straps are hemmed or fused together on either side of each of the three pathways, forming the three pathways therein.

According to one aspect, in an assembled configuration, the elongate strap is configured to conform to the user's upper body anatomy. According to one aspect, the elongate strap has a width between 1.0 inches and 2.5 inches. According to one aspect, the elongate strap comprises an elastic strap.

According to one aspect, the device further includes at least three additional pieces of material attached to the elastic strap, each piece of material forming one of the at least three pathways between a surface of the piece of material and an opposing surface of the elastic strap.

According to one aspect, in an assembled configuration, the elongate strap is configured to have a portion of the elongate strap disposed within one of the at least three pathways such that the elongate strap comprising the pathway is perpendicular to the portion of the elongate strap disposed within the pathway.

According to one aspect, none of the at least three pathways extends from the first edge to the second edge in parallel to another of the at least three pathways. According to one aspect, each pathway of the at least three pathways is formed by a pair of parallel seams extending linearly from the first edge to the second edge.

According to one aspect, in an assembled configuration, the elongate strap is configured to have a portion of the elongate strap disposed between each pair of parallel seams. According to one aspect, the elongate strap comprises one of neoprene, foam, elastic, webbing, and lace.

According to one aspect of the invention, a method for supporting posture includes arranging an elongate strap to form a plurality of loops with two loose ends; positioning the loops around arms and shoulders of a user; securing the loose ends on a front of the user's torso; and separating portions of the elongate strap arranged at the user's shoulder to increase a surface area of the elongate strap contacting the user's shoulders.

According to one aspect, the method further includes pulling the loose ends down and away from the user's torso to tighten the plurality of loops prior to securing the loose ends in front of the user's torso. According to one aspect, the method further includes threading the elongate strap through a plurality of pathways formed in the elongate strap such that an orientation of each of the plurality of pathways determines an orientation of the portion of the elongate strap threaded through the pathway with respect to the portion of the elongate strap forming the pathway.

BRIEF DESCRIPTION OF THE DRAWINGS

Further objectives and advantages will become apparent from a consideration of the description, drawings, and examples.

FIG. 1A shows the posture support device in its unassembled state, not yet in use, in one embodiment of the invention, seen from the side (cross-sectional view).

FIG. 13 shows a step of a step-by-step process of assembling the garment.

FIG. 14 shows another step of a step-by-step process of assembling the garment.

FIG. 14A shows another step of a step-by-step process of assembling the garment.

FIG. 15 shows another step of a step-by-step process of assembling the garment.

FIG. 16 shows another configuration (with multiple straps) of the posture support device in its assembled state, on the body of an individual, observing the front of person wearing it.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

A posture support device uses straps that conform to the upper body's anatomy and shape to provide support for a healthier and better-aligned posture. The design of the device promotes improved posture by gently retracting the shoulders to promote proper alignment of the upper back, neck, and shoulders, thereby preventing postural problems and easing discomfort from tension and strain. An objective of this invention according to one aspect is to bring about proper spinal alignment by gently retracting the shoulders, reducing cervical stress and strain as well as associated pains. Other objectives include: ease of use without the need for assistance by another person to put on the device, to remove the device, and to adjust the device to the wearer's particular body size, shape, and preference.

Figure 1:
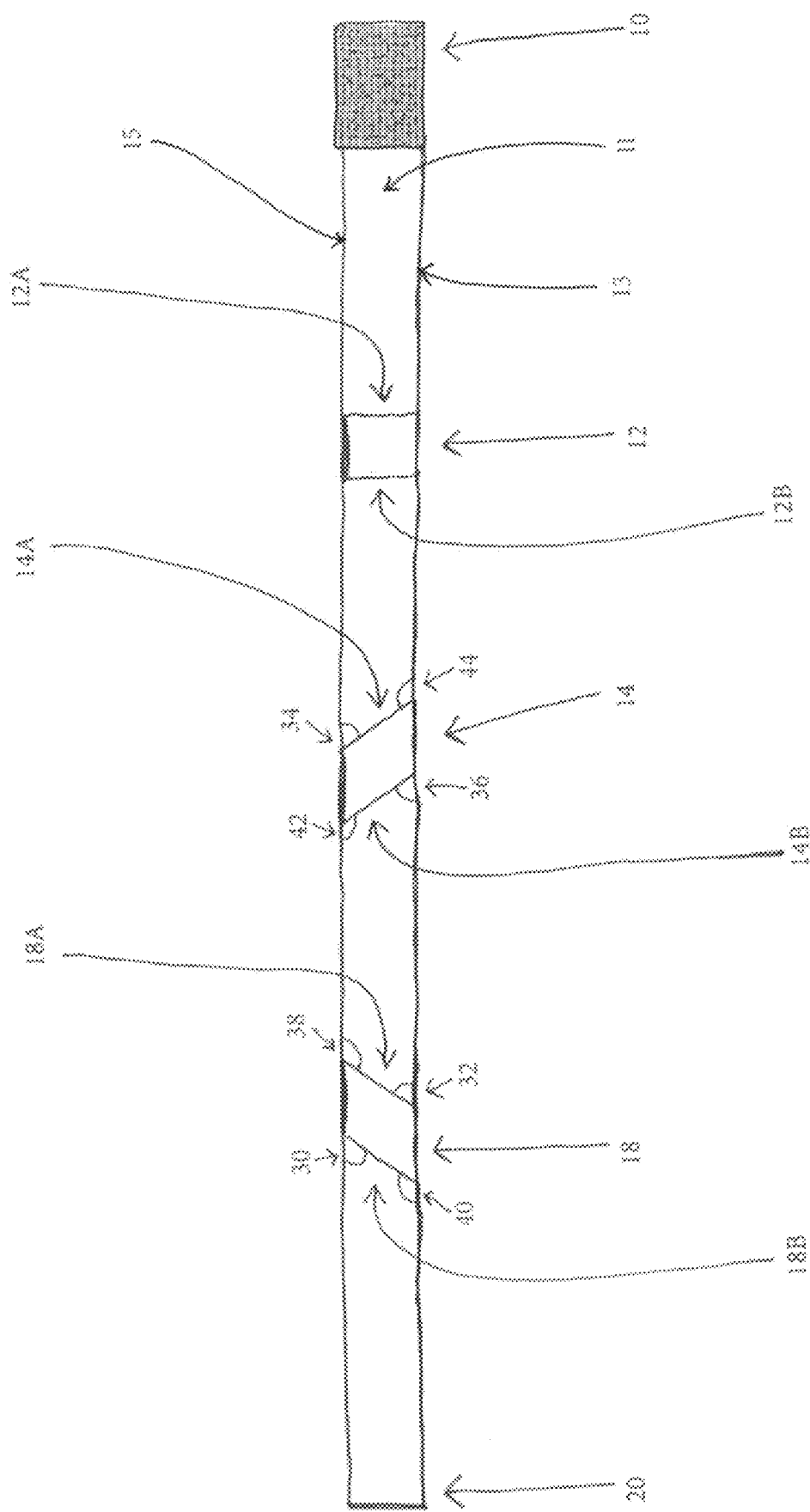
FIG. 1 shows the posture support device in its unassembled state, not yet in use, in one embodiment of the invention, seen from the front (straight on view).

A posture support device according to one aspect of the invention is shown in FIG. 1. The posture support device includes an elongate strap having: a first end 10 comprising a first fastening member; a second end 20 comprising a second fastening member; a first surface 11 extending from the first end 10 to the second end 20; a second surface (back side, not shown in FIG. 1) extending from the first end 10 to the second end 20; a first edge 13 extending from the first end 10 to the second end 20 along a first side of the first surface 11 and the second surface; and a second edge 15 extending from the first end 10 to the second end 20 along a second side of the first surface 11 and the second surface, the second side being opposite the first side. The elongate strap comprises at least three pathways 12, 14, 18 formed therein, each pathway 12, 14, 18 extending from the first edge 13 to the second edge 15 between the first surface 11 and the second surface. In an assembled configuration, the elongate strap is configured to have a portion of the elongate strap disposed within each of the at least three pathways 12, 14, 18 and to have the first and second fastening members secured to form the posture support device.

According to one aspect, a first pathway 12 of the at least three pathways 12, 14, 18 extends perpendicular to the first edge 13 and the second edge 15. According to one aspect, a second pathway 14 and a third pathway 18 of the at least three pathways 12, 14, 18 do not extend perpendicular to the first edge and the second edge. According to one aspect, each of the at least three pathways 12, 14, 18 has a width that is between 100% and 150% the width of the elongate strap. The width of the elongate strap may be defined as the distance between the first edge 13 and the second edge 15.

According to one aspect, in an assembled configuration, the elongate strap is configured to have a portion of the elongate strap disposed within the pathway 12 such that the elongate strap comprising the pathway 12 is perpendicular to the portion of the elongate strap disposed within the pathway 12.

According to one aspect, none of the at least three pathways 12, 14, 18 extends from the first edge 13 to the second edge 15 in parallel to another of the at least three pathways 12, 14, 18.

As shown in FIG. 1, a posture support device according to one aspect of the invention includes an elongate strap having: a first end 10 comprising a first fastening member; a second end 20 comprising a second fastening member; a first surface 11 extending from the first end 10 to the second end 20; a second surface (back side, not shown in FIG. 1) extending from the first end 10 to the second end 20; a first edge 13 extending from the first end 10 to the second end 20 along a first side of the first surface 11 and the second surface; and a second edge 15 extending from the first end 10 to the second end 20 along a second side of the first surface 11 and the second surface, the second side being opposite the first side. The elongate strap comprises at least three pathways 12, 14, 18 formed therein. Each of the at least three pathways 12, 14, 18 forms a different angle with respect to one of the first edge or the second edge with than the other two of the at least three pathways 12, 14, 18. For example, in FIG. 1, each of the three passageways 12, 14, and 18 is angled uniquely with respect to the first edge 13.

In an assembled configuration, the elongate strap is configured to have a portion of the elongate strap disposed within each of the at least three pathways 12, 14, 18 and to have the first and second fastening members secured to form the posture support device.

Figure 4:
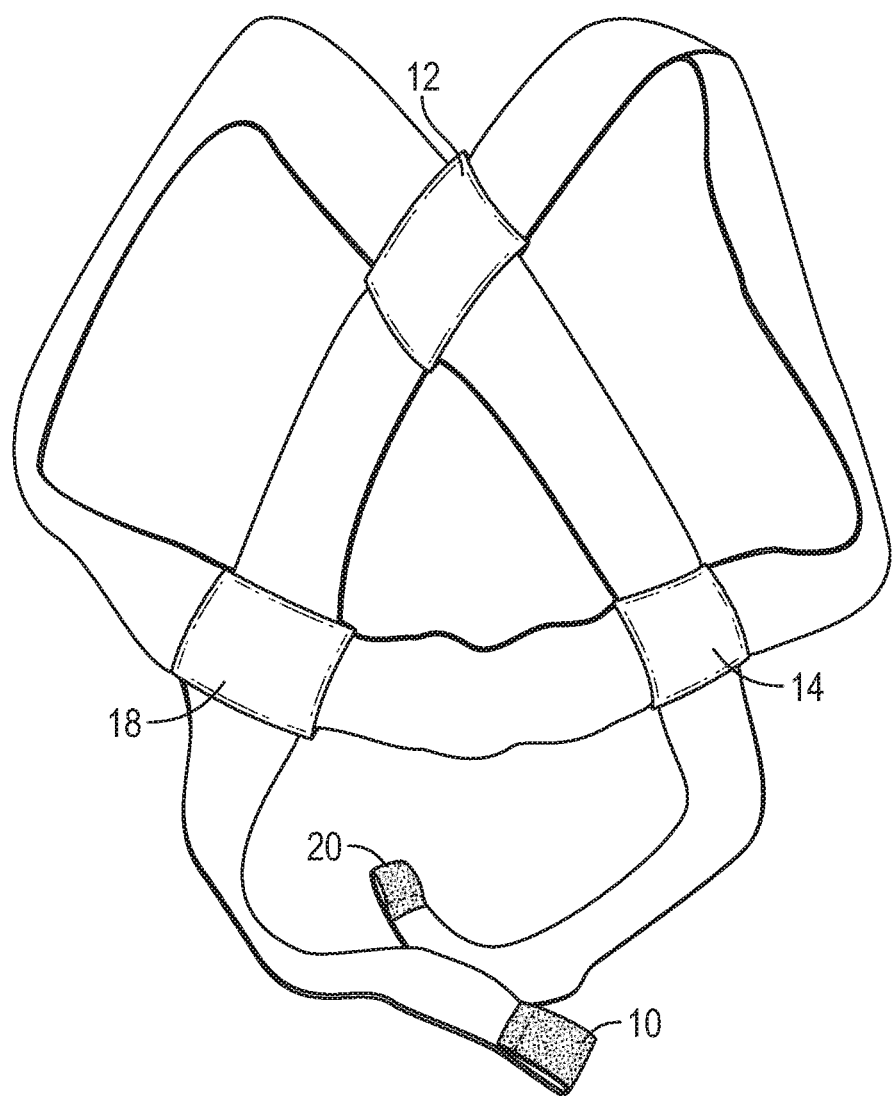
FIG. 4 shows the posture support device in its assembled state, however not yet on the body of an individual, seen from the front.
Figure 5:
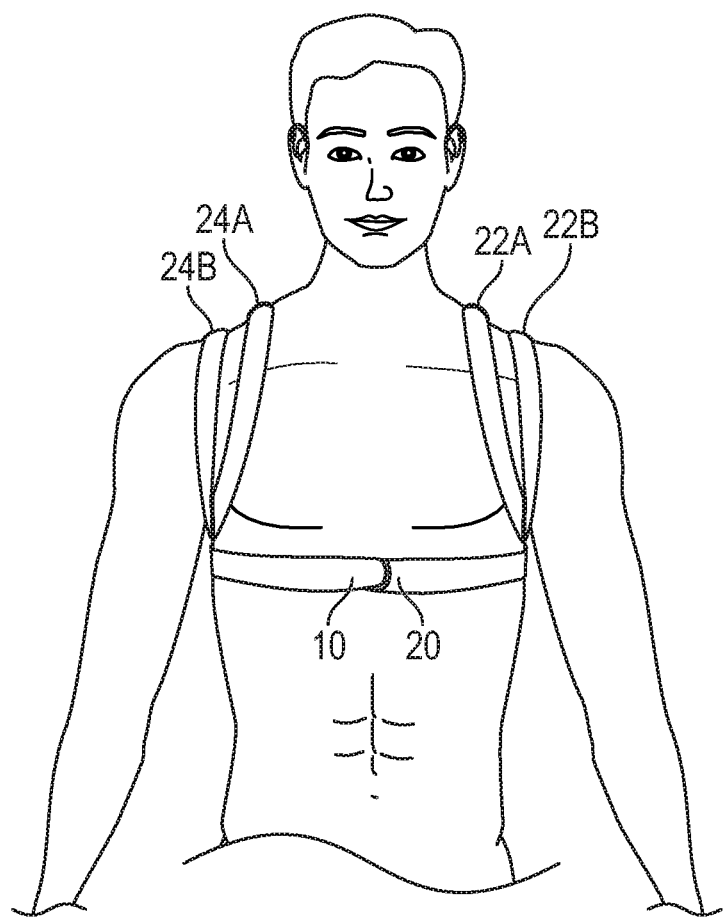
FIG. 5 shows the posture support device in its assembled state, on the body of an individual, observing the front of the person wearing it.
Figure 10:
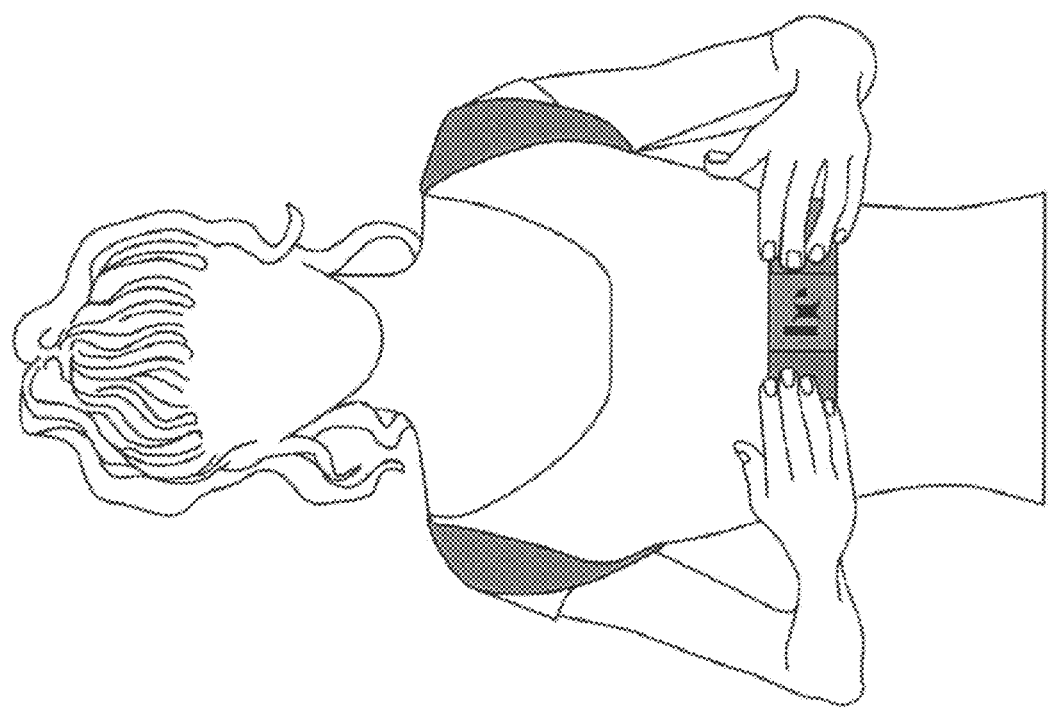
FIG. 10 shows another step of a step-by-step process of a wearer putting on and adjusting the garment to the wearer's body.

The posture support device according to one aspect is a band comprising two soft, elasticized straps of equal length sewn together at certain points 10, 12A, 12B, 14A, 14B, 18A, 18B, and 20 as seen in FIGS. 1 and 1A. When assembled and worn as seen in FIGS. 5 and 10, the two ends of the band 10 and 20 are joined together by fastening members, this is seen in FIG. 4.

Figure 2:
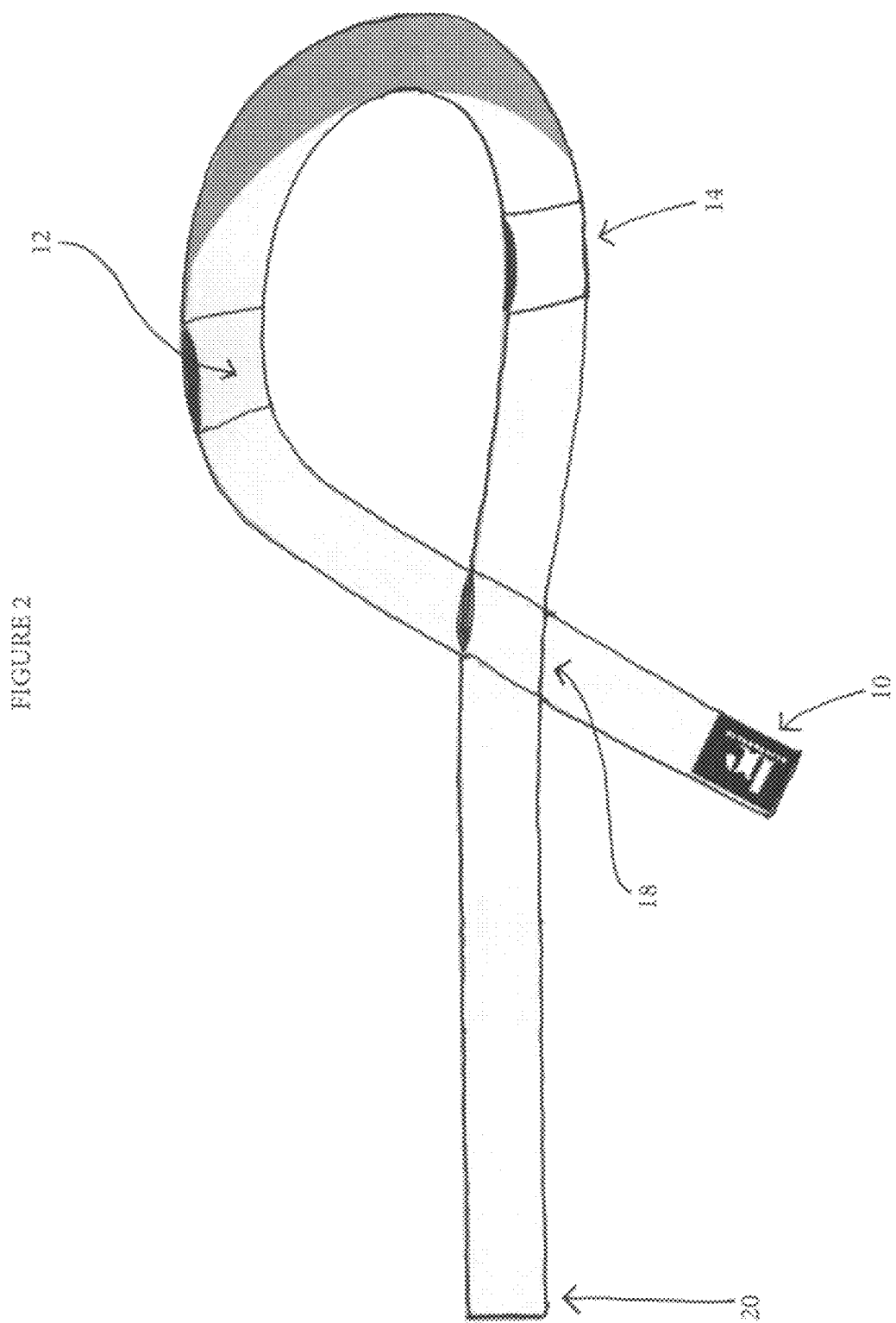
FIG. 2 shows a step of assembly of the posture support device.
Figure 3:
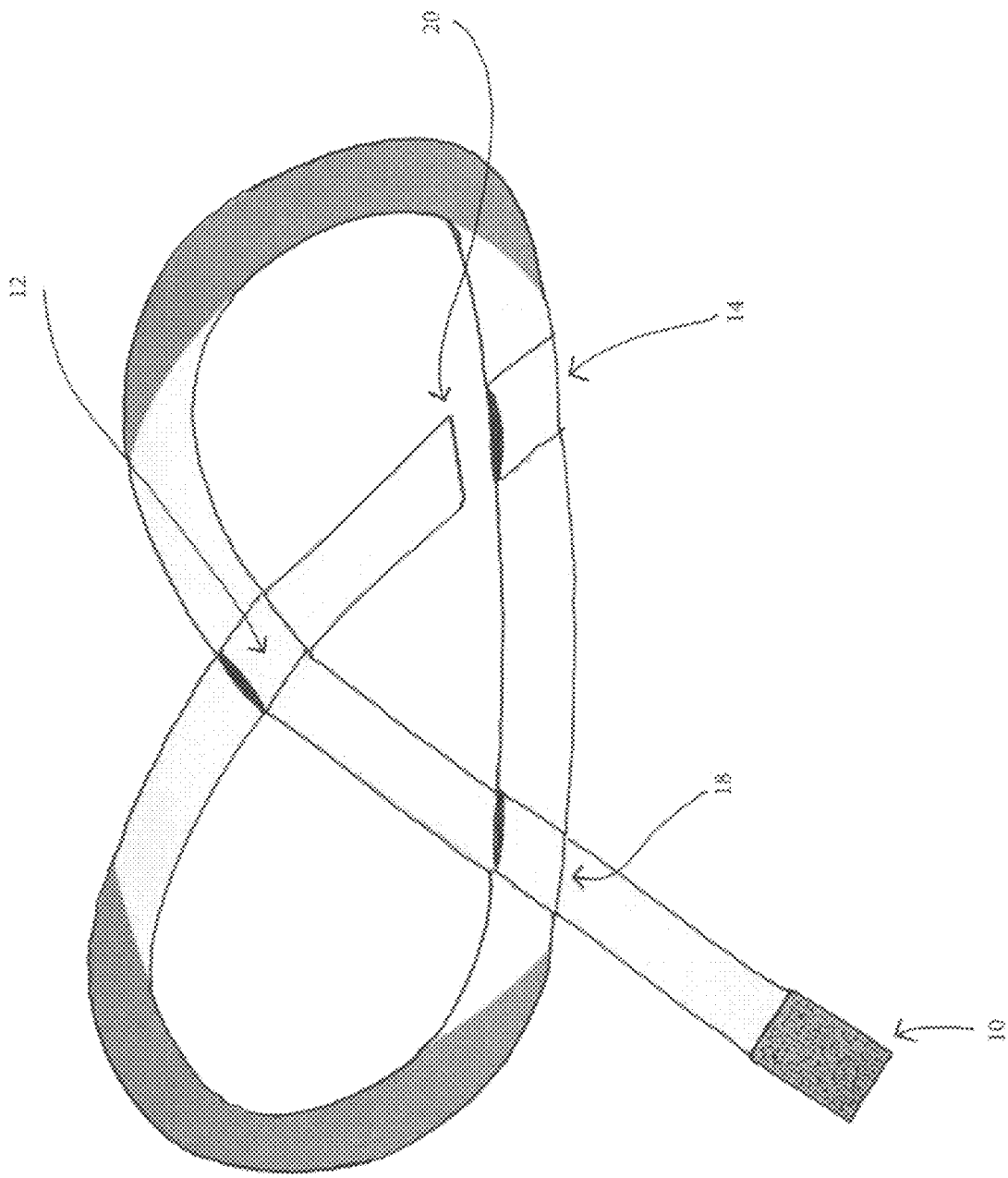
FIG. 3 shows another step of assembly of the posture support device.
Figure 6:
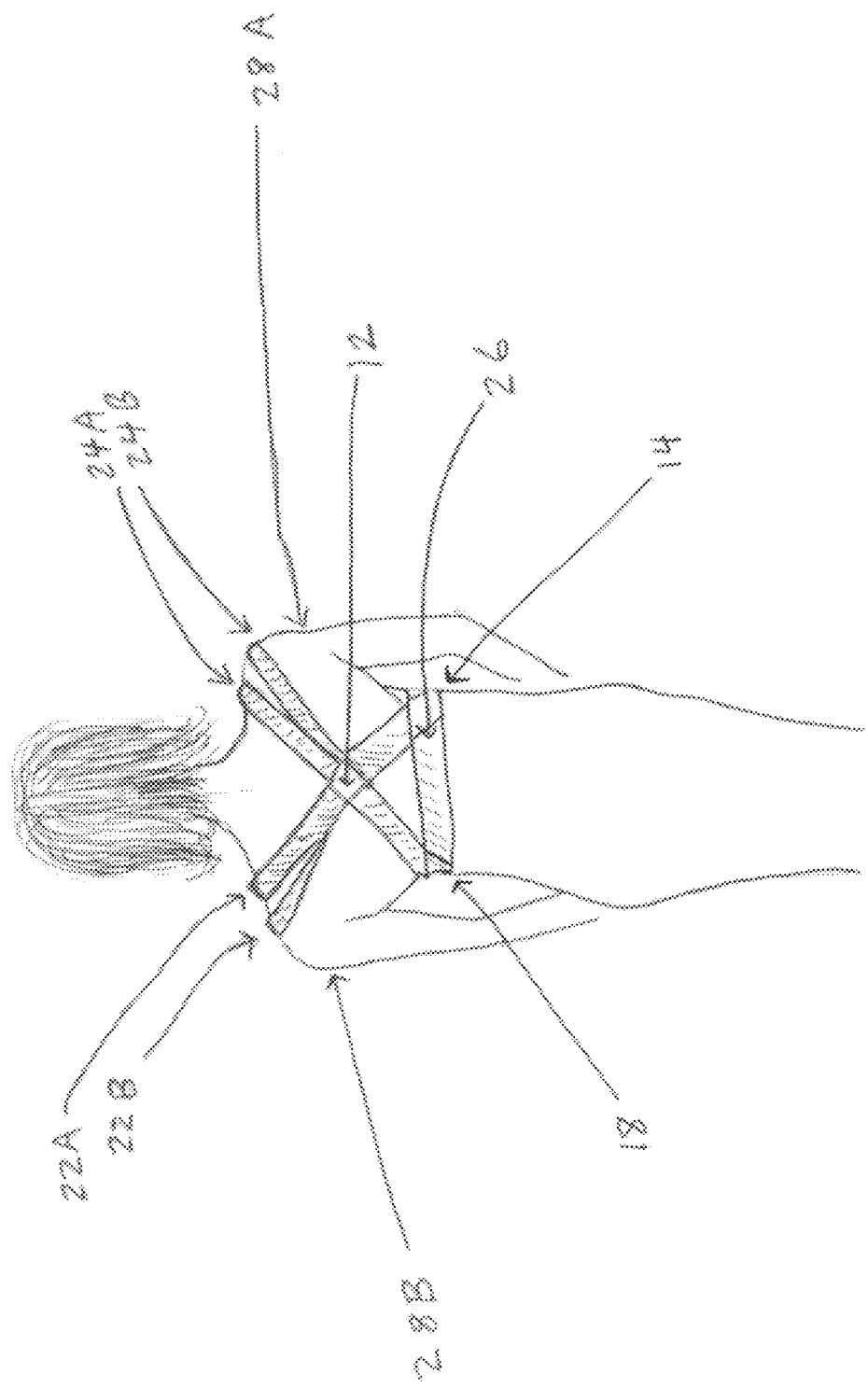
FIG. 6 shows the posture support device in its assembled state, on the body of an individual, observing the back of the person wearing it.

During the assembly of the product as seen in FIGS. 2, 3, 13, 14, and 14A, each end of the band 10 and 20 is threaded through openings (also referred to herein as "pathways") 18, 12, and 14, in a crisscross fashion that provides the form and shape of the wearable device. The crisscross "x" (i.e., the intersection point) occurs at the opening 12 as shown in FIGS. 3, 4, 6, 8, 14, 14A, 15, and 15A and serves as one of three points of leverage as shown in FIG. 6 on the wearer's shoulders 28A and 28B and upper back producing a supplementary scapular effect (i.e., assistance in retracting the shoulders). The openings 14 and 18, which are also shown in FIG. 3, serve as additional points of leverage working in conjunction to counteract the elevation and forward positioning of the shoulders.

The angled parallel seams 14A, 14B, 18A, and 18B shown in FIG. 1 form the openings 14 and 18, enabling each end of the band 10 and 20 to be threaded through openings 14, 12, and 18 at the optimal angle to effectively retract the shoulders, depress the scapula, and stabilize the base of the scapular line 26 in FIG. 6. As seen in FIG. 5, each end of the band 10 and 20 is wrapped around the wearer's rib cage or lower chest and then is connected to the other (e.g., with first and second fastening members).

FIG. 1 illustrates the band (i.e., comprising two elasticized straps connected together at specific points) when the band has not yet been assembled into its wearable form. FIG. 1 shows the inside side of the band (i.e., the side of the band which will be against the skin of the wearer) seen in a straight on view. On the right side of FIG. 1 a fasting member at the end-piece of the band 10 will attach to a fastening member at the other end piece 20 when the band is assembled.

The distance of the band 10 to 20 may range from 36 inches to 154 inches. The width of the straps may range between 1 inch and 2.5 inches.

On the right side of FIG. 1 are two seams 12A and 12B, that are parallel to one another and are perpendicular to the band. Seams 12A and 12B attach the two straps to create the band and also create the opening 12 through which one end of the band 20 will pass. The distance between 10 and 12A may range from 8 inches to 33 inches. In one configuration, the distance between 10 and 12A is approximately 22% of the entire length of the band. The distance between 12A and 12B (i.e., location 12) may range from 1 inch to 4 inches. In one configuration, the distance between 12A and 12B is approximately 3% of the entire length of the band. According to one aspect, the distance between 12A and 12B is between 100% and 150% the width of the band. The distance between 12B and 14A may range from 6 inches to 30 inches. In one configuration, the distance between 12B and 14A is approximately 18% of the entire length of the band.

Parallel seams 14A and 14B also attach the two straps to create the band and are angled diagonally to the band in a "back slash" diagonal line. The distance between 14A and 14B (i.e., location 14) may range from 1 inch to 4 inches. In one configuration, the distance between 14A and 14B is approximately 3% of the entire length of the band. According to one aspect, the distance between 14A and 14B is between 100% and 150% the width of the elongate strap. The distance between 14B and 18A may range between 3 inches and 14 inches. In one configuration, the distance between 14B and 18A is approximately 9% of the entire length of the band.

Parallel seams 18A and 18B also attach the two straps to create the band and are diagonal to the band in a "forward slash" diagonal line. The distance between 18A and 18B (i.e., location 18) may range from 1 inch to 4 inches. In one configuration, the distance between 18A and 18B is approximately 3% of the entire length of the band. According to one aspect, the distance between 18A and 18B is between 100% and 150% the width of the elongate strap. The distance between 18B and 20 may range from 16 inches to 65 inches. In one configuration, the distance between 18B and 20 is approximately 43% of the entire length of the band.

The diagonally angled parallel seams 14A, 14B, 18A, and 18B that create openings 14 and 18 (passageways through which the ends of the band 10 and 20 will pass) are specifically configured to more effectively align and contour to the body of the wearer as seen in FIG. 6. The way in which the ends of the band 10 and 20 pass through openings 14 and 18 at diagonal angles as seen in FIGS. 3 and 6 and then wraps around the ribcage of the wearer, provides increased leverage allowing the device to more effectively resist forward motion of the wearers' shoulders. Because the width of the openings 14 and 18 is only slightly larger than the width of the band, the orientation of openings 14 and 18 determines the orientation of the portion of the band threaded through the openings 14 and 18 with respect to the portion of the band forming the pathway. The openings 14 and 18 thus help maintain the desired relative alignment of the portions of the band during use.

Underneath the band at location 20 of FIG. 1, not facing the viewer in the perspective of FIG. 1, is the corresponding end-piece of the band that will attach or adhere to the other end piece 10 (e.g., by corresponding fastening members) when the band is assembled.

In some configurations, angles 30 and 32 formed by seams 18B and 18A respectively, are congruent angles, as are angles 34 and 36 which are formed by seams 14A and 14B respectively.

In some configurations, angles 38 and 40 formed by seams 18A and 18B respectively, are congruent angles, as are angles 42 and 44 which are formed by seams 14B and 14A respectively. Additionally, angles 30 and 34 may be corresponding congruent angles, angles 38 and 42 may be corresponding congruent angles, angles 40 and 44 may be corresponding congruent angles, and angles 32 and 46 may be corresponding congruent angles. Angles 30, 32, 34, and 36 may range between 40 degrees and 90 degrees, between 45 and 80 degrees, or between 50 and 70 degrees. Angles 38, 40, 42, and 44 may range between 90 degrees and 140 degrees, between 100 degrees and 135 degrees, or between 110 degrees and 130 degrees.

As seen in FIG. 1A in a cross-sectional view, the band includes two elasticized straps which are attached at end-points 10 and 20. Location 12A and location 12B indicate the seam locations for the opening 12. Location 14A and 14B indicate the seam locations for the opening 14. Location 18A and location 18B indicate the seam locations for the opening 18. The specific relative placement of the seams (i.e., openings 12, 14, and 18) along the length of band is vital to the proper fit of the device.

The way in which the device is constructed to wrap around the front of the chest provides increased stability as well as simplified adjustability.

The specific placement and relative distances between the endpoints of the band 10 and 20 and the seams 12A, 12B, 14A, 14B, 18A, and 18B is crucial to the construction and functionality of the device. These proportionate distances are what allow the device to fit the body of the wearer in a way that provides maximum support and leverage.

FIG. 2 illustrates the posture support device that was seen in FIG. 1, except that the right side of the band 10 has been moved and slid through opening 18.

FIG. 3 illustrates the posture support device that was seen in FIG. 2, except that the left side of the band 20 has been moved and slid through opening 12 and through opening 14.

FIG. 4 illustrates the posture support device that was seen in FIG. 3, except that the two end-pieces 10 and 20 have been attached (e.g., by fastening members).

FIG. 5 illustrates the posture support device that was seen in FIG. 4 being worn by an individual with the end-pieces 10 and 20 attached and fastened with the posture support device fully assembled.

FIG. 6 illustrates the posture support device being worn by an individual, as seen from behind the person wearing it. The double strap or split strap system 22A and 22B on one side and 24A and 24B on the other side, spread across the shoulders 28A and 28B of the wearer, provides support that is adjustable and that allows for shoulder and arm mobility. The configuration of the split straps 22A and 22B, 24A and 24B in conjunction with the placement of the band supporting the base of the wearer's scapula 26, function as a 3-point leverage system, forming a triangle which reinforces the stabilizing function of the shoulder blades 28A and 28B.

It is also easily adjustable due to the fact that the posture support device has only one connection point which consists of the two ends of the band 10 and 20.

Figure 11:
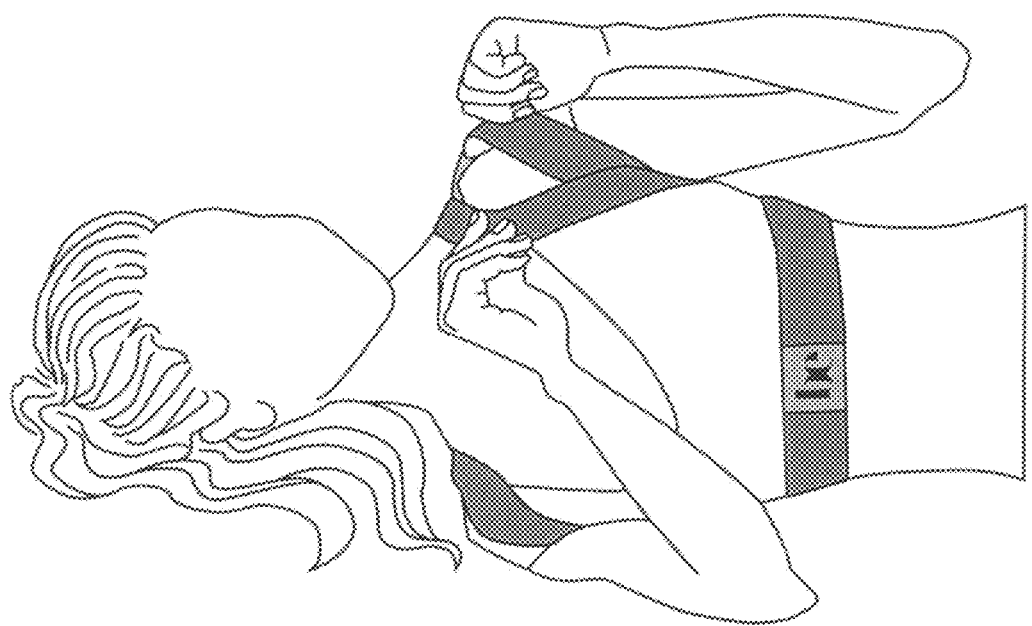
FIG. 11 shows another step of a step-by-step process of a wearer putting on and adjusting the garment to the wearer's body.

The benefits of having two straps as seen in FIG. 1A comprising the band include: increased tensile strength and flex to the band, which creates resistance to counteract hunching of the shoulders; natural gaps or openings between the straps, which enable the ends of the band 10 and 20 to be threaded through openings 12, 14, 18 giving the device its supportive structure; ease of use to adjust the straps 22A, 22B, 24A and 24B at the shoulders 28A and 28B for customized comfort as seen in FIGS. 6 and 11.

The benefits of having the two straps sewn or otherwise connected together at specific points, with openings or gaps in between, as opposed to the two straps sewn or connected together completely without openings or gaps, include: that the sections of the band between openings 12 and 14 and between openings 18 and 20 as seen in FIG. 1, can wrap around the shoulders of the wearer as seen in FIGS. 6 and 11 and, by virtue of being unattached to each other in those sections, can enable the wearer to separate the two straps 22A, 22B, 24A and 24B to cover, as desired, more or less surface area around the wearer's shoulders (see FIG. 11) thereby providing varying levels of support and customization of the fit; that without the straps being fully attached there is increased flexibility without losing tensile strength; and that, by having openings or gaps there is more aeration, and so the band is more hygienic and is easier to wash than a completely sealed band.

Figure 7:
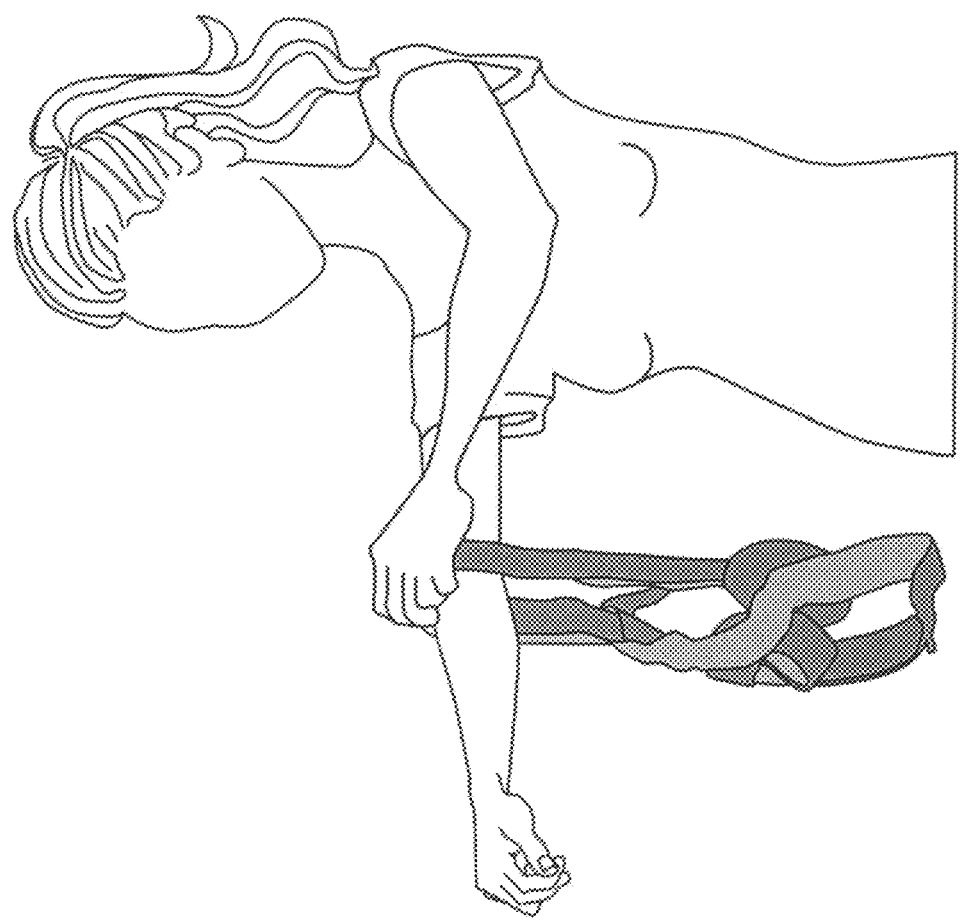
FIG. 7 shows a step of a step-by-step process of a wearer putting on and adjusting the garment to the wearer's body.
Figure 8:
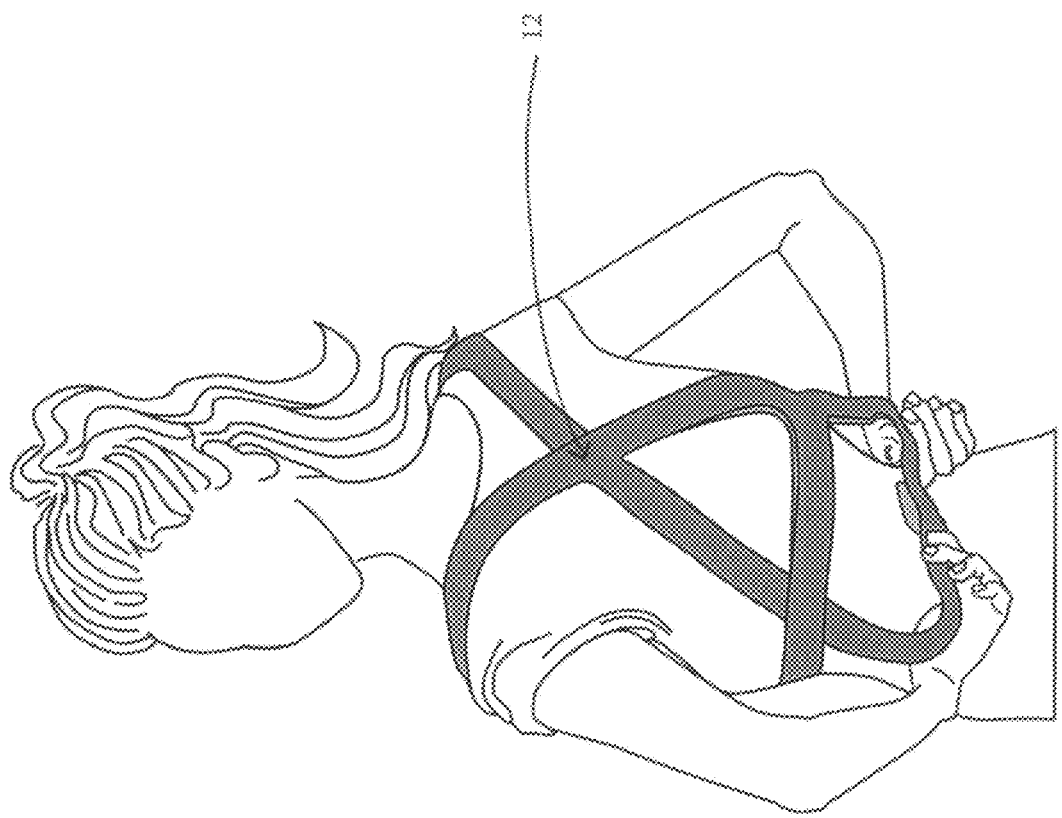
FIG. 8 shows another step of a step-by-step process of a wearer putting on and adjusting the garment to the wearer's body.
Figure 9:
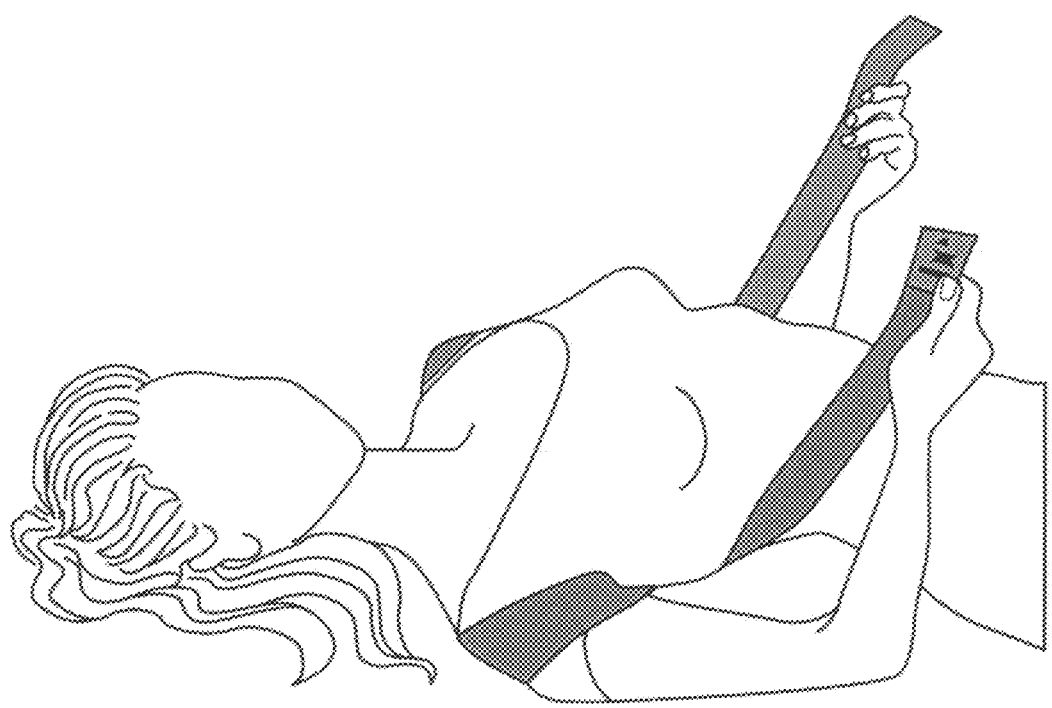
FIG. 9 shows another step of a step-by-step process of a wearer putting on and adjusting the garment to the wearer's body.

FIGS. 7-11 depict the step-by-step process of a wearer putting on and adjusting the garment to the wearer's body. As seen in FIG. 7, the wearer puts on the posture support device as though putting on a vest as the straps wrap around the shoulders and join at intersection 12 forming an "x" shape across the back as seen in FIG. 8. As seen in FIG. 9, the wearer stretches and pulls each end of the band down and away from the wearer, by the wearer pulling each end of the band in a slightly downward direction and then wrapping each end of the band around the wearer's chest, and then, where the end-points meet, the wearer joins them together as seen in FIG. 10 (as each end of the band will join with the other end, by means of one or more fastening members).

Figure 15A:
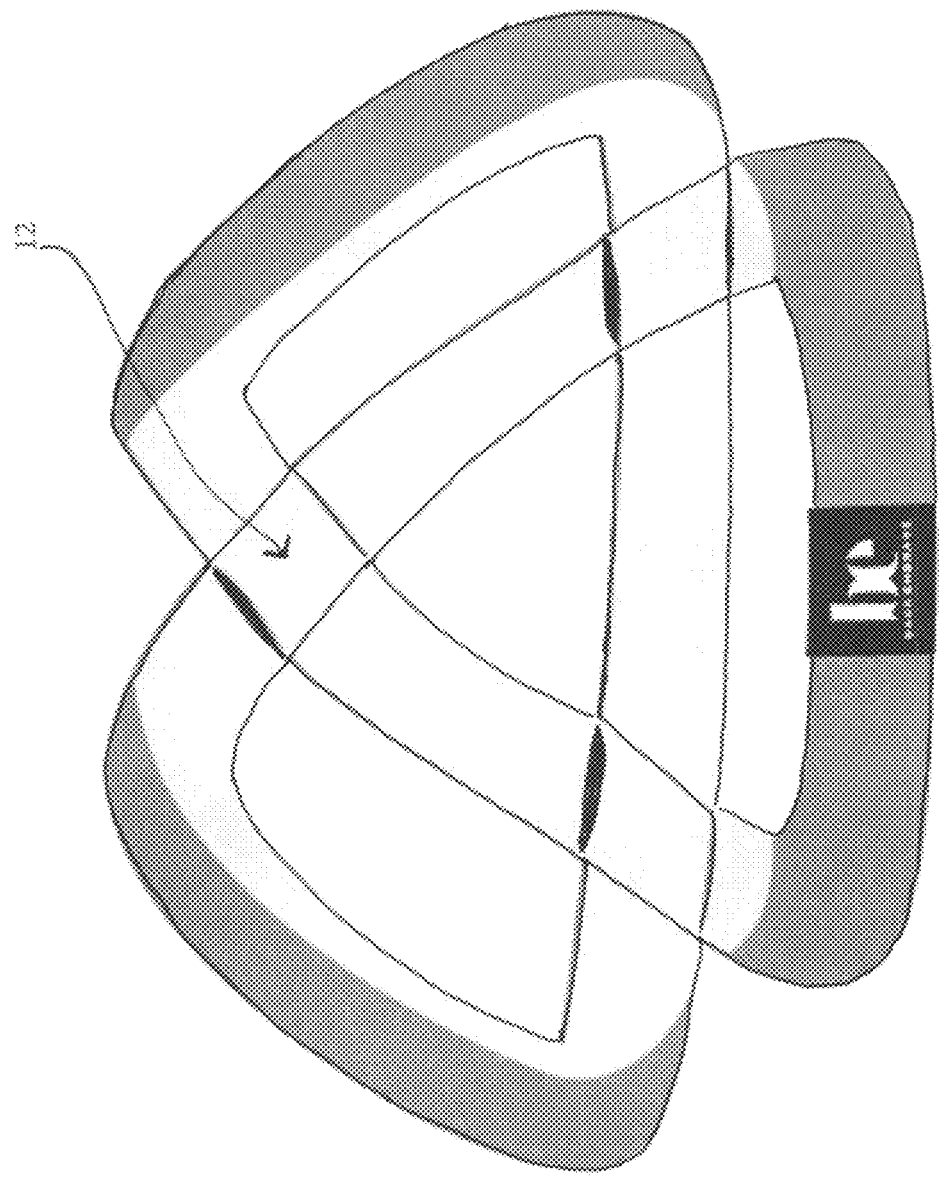
FIG. 15A shows another step of a step-by-step process of assembling the garment.

FIGS. 12-15A demonstrate the assembly of the posture support device according to one aspect of the invention. The user first lays out the posture support device with the logo face down on the user's righthand side as seen in FIG. 12A. The user then folds the logo on the righthand side so that the BE logo now faces up (this allows the end 10 to slide more easily through opening 18 without the hook portion of the fastening member (e.g., Velcro®) snagging the straps) as seen in FIG. 12B. Next, as seen in FIG. 13, the user takes the end on the righthand side 10 and slides it from the upper right to the lower left through opening 18 approximately five inches. Now that the band has been passed through opening 18, the user unfolds the end piece 10, so that the hook portion of the fastening member is exposed and facing up. As seen in FIG. 14A, the user takes the end on the left 20, (keeping the loop portion of the fastening member facing down) and slides it from upper left to lower right through opening 12 and then continues sliding it through opening 14 approximately five inches. FIG. 15 shows the last step in the assembly of the device before the user secures ends 10 and 20 together. As seen in FIG. 15A, the posture support device is fully assembled and ready to be worn.

FIG. 16 illustrates another embodiment of the invention being worn by an individual; in this embodiment there are multiple straps wrapping around each shoulder, instead of having two straps per shoulder as illustrated and described in the previously described embodiment.

Alternative embodiments also include but are not limited to: embedding the posture support device into other garments such as undergarments and/or garments such as a jacket, incorporating the posture support device into a corset-like garment and connecting the device to a lower back posture support device.

Figure 12:
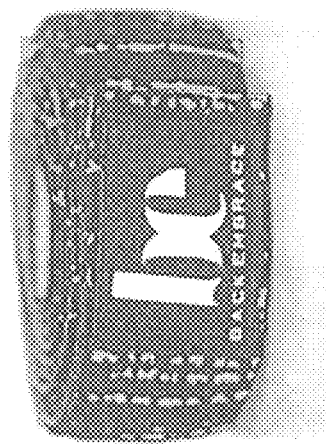
FIG. 12 shows the posture support device unassembled and rolled up.
Figure 12A:
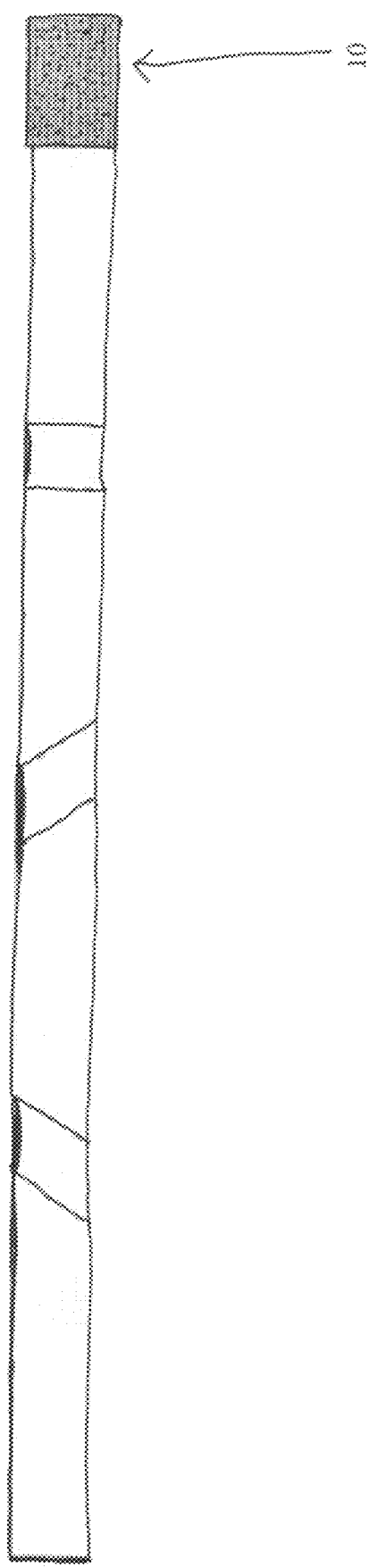
FIG. 12A show the posture support device unassembled and laid out according to one aspect.
Figure 12B:
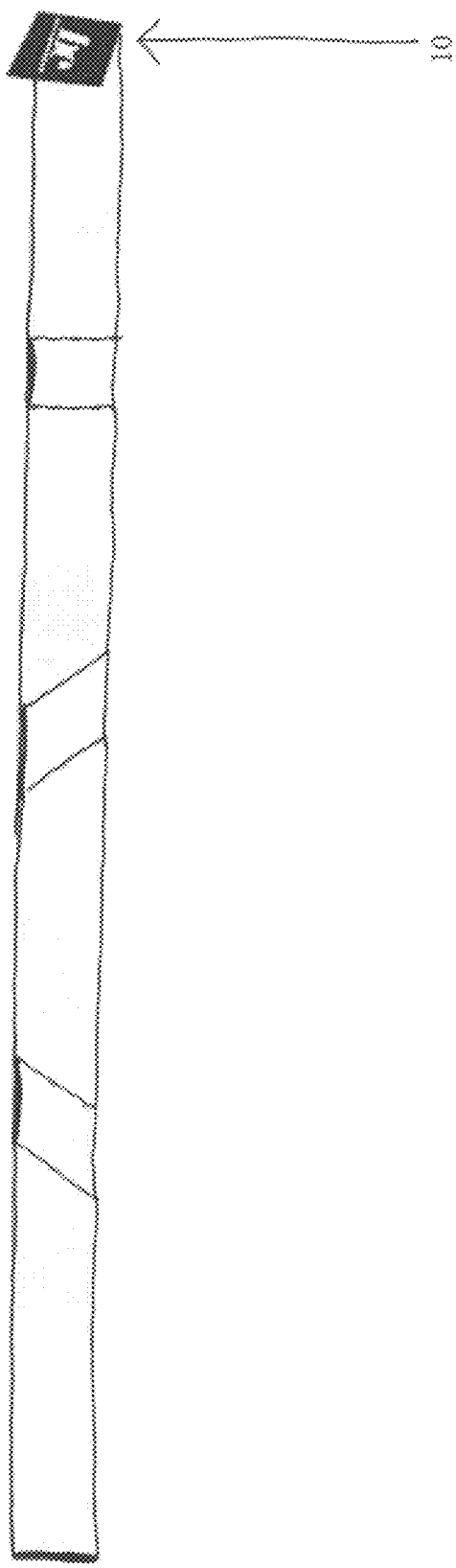
FIG. 12B shows the posture support device unassembled and laid out according to another aspect.

In its unassembled state as seen in FIG. 1, the posture support device may be used in other settings to stretch the human body or as a strengthening tool, making it versatile for other uses, and it can be easily wrapped/rolled up and put away as seen in FIG. 12.

The flexible nature of the material assists in making the device easily adjustable to accommodate different body shapes and sizes and also enables the pressure (to retract the shoulders) to be more evenly distributed over the wearer's shoulders. It is especially important that the underside of the straps that make up the underside of the band (i.e., the side in direct contact with the skin or body of the wearer) be constructed with a soft material non-abrasive and non-irritating to the skin as to prevent chaffing and/or irritation. The material used to construct the device may be a hybrid of materials that provides resistance as well as flexibility. The following materials may be used, a combination thereof, or any alternative material(s) effective in providing resistance, softness, and flexibility: neoprene, foam, elastic, webbing, and/or lace. Any such material(s) also may be reinforced by the following material/s and/or material(s) containing such properties: wire, cording, and/or silicone. Such material(s) may also be embedded with magnets due to their healing qualities. Additionally, the material(s) may contain cooling properties, with the intended effect being to reduce inflammation in the body. Such material(s) may be infused with fragrance beads or scented materials intended to promote the overall wellbeing of the wearer. The material(s) may incorporate reflective or reflective-type material or contain reflective-type components such as patches or stickers that provide increased visibility and thereby promote safety for the wearer when worn outdoors or after dark or while performing such activities such as bike riding.

The bands may be joined by use of one or more fastening members. For example, the fastening member may be a magnet, a tie, a fastener or variation thereof such a clasp, clip, hook, buckle, or hook and loop. The fastening member may have a hook and loop structure such as, for example, Velcro®. The fastening member may have identical members on each end of the posture support device, or may have complementary members, such as hook structures on one end and loop structures on the other end, for example.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. Moreover, features described in connection with one embodiment of the invention may be used in conjunction with other embodiments, even if not explicitly stated above. It is therefore to be understood that, within the scope of the claims and their equivalents, the invention may be practiced otherwise than as specifically described.

I claim:

1. A posture support device comprising:
   an elongate strap having:
   a first end comprising a first fastening member;
   a second end comprising a second fastening member;
   a first surface extending from the first end to the second end;
   a second surface extending from the first end to the second end;
   a first edge extending from the first end to the second end along a first side of the first surface and the second surface; and
   a second edge extending from the first end to the second end along a second side of the first surface and the second surface, the second side being opposite the first side,
   wherein the elongate strap comprises at least three pathways comprising openings, each pathway extending from the first edge to the second edge between the first surface and the second surface, wherein each of the at least three pathways is defined by a set of parallel seams arranged in the elongate strap, wherein a first set of parallel seams defining a first pathway are perpendicular to the first edge and the second edge, and wherein a second set of parallel seams defining a second pathway are diagonally angled between the first edge and the second edge,
   wherein, in an assembled configuration, the elongate strap is configured to have a portion of the elongate strap disposed within each of the at least three pathways and to have the first and second fastening members secured to form the posture support device, and
   wherein the elongate strap comprises split straps configured to be arranged at each of the user's shoulders, wherein the split straps comprise a first split strap having two straps configured to be arranged at a user's first shoulder and a second split strap having two straps configured to be arranged at a user's second shoulder.

2. The posture support device according to claim 1, wherein the first pathway of the at least three pathways extends perpendicular to the first edge and the second edge.

3. The posture support device according to claim 1, wherein the second pathway and a third pathway of the at least three pathways do not extend perpendicular to the first edge and the second edge.

4. The posture support device according to claim 1, wherein each of the at least three pathways has a width that is between 100% and 150% the width of the elongate strap.

5. The posture support device according to claim 1, wherein, in an assembled configuration, an angle of the portion of the elongate strap disposed within each of the at least three pathways is determined by an angle of each of the at least three pathways.

6. The posture support device according to claim 1, wherein the elongate strap is two parallel straps, wherein the at least three pathways are formed between opposing inner surfaces of the two parallel straps.

7. The posture support device according to claim 6, wherein the two parallel straps are joined only at the first end, the second end, and on either side of each of the at least three pathways.

8. The posture support device according to claim 6, wherein the two parallel straps are hemmed or fused together on either side of each of the at least three pathways, forming the at least three pathways therein.

9. The posture support device according to claim 1 wherein, in an assembled configuration, the elongate strap is configured to conform to the user's upper body anatomy.

10. The posture support device according to claim 1, wherein the elongate strap has a width between 1.0 inches and 2.5 inches.

11. The posture support device according to claim 1, wherein the elongate strap comprises an elastic strap.

12. The posture support device according to claim 11, further comprising at least three additional pieces of material attached to the elastic strap, each piece of material forming one of the at least three pathways between a surface of the piece of material and an opposing surface of the elastic strap.

13. The posture support device according to claim 1, wherein, in an assembled configuration, the elongate strap is configured to have a portion of the elongate strap disposed within one of the at least three pathways such that the elongate strap comprising the one of the at least three pathways is perpendicular to the portion of the elongate strap disposed within the one of the at least three pathways.

14. The posture support device according to claim 1, wherein none of the at least three pathways extends from the first edge to the second edge in parallel to another of the at least three pathways.

15. The posture support device according to claim 1, wherein each of the sets of parallel seams extends linearly from the first edge to the second edge.

16. The posture support device according to claim 15, wherein in an assembled configuration, the elongate strap is configured to have a portion of the elongate strap disposed between each pair of parallel seams.

17. The posture support device according to claim 1, wherein the elongate strap comprises one of neoprene, foam, elastic, webbing, and lace.

18. A method for supporting posture, comprising:
   arranging an elongate strap to form a plurality of loops with two loose ends;

positioning the plurality of loops around arms and shoulders of a user;

securing the loose ends on a front of the user's torso;

separating two straps of the elongate strap arranged at a user's first shoulder to increase a first surface area of the elongate strap contacting the user's first shoulder;

separating two straps of the elongate strap arranged at a user's second shoulder to increase a second surface area of the elongate strap contacting the user's second shoulder; and threading the elongate strap through a plurality of pathways comprising openings in the elongate strap defined by a plurality of sets of parallel seams arranged in the elongate strap, wherein a first set of parallel seams defining a first pathway are perpendicular to a first edge of the elongate strap and a second edge of the elongate strap, and wherein a second set of parallel seams defining a second pathway are diagonally angled between the first edge and the second edge.

19. The method for supporting posture according to claim 18, further comprising:

pulling the loose ends down and away from the user's torso to tighten the plurality of loops prior to securing the loose ends in front of the user's torso.

20. The method for supporting posture according to claim 18, further comprising:

threading the elongate strap through the plurality of pathways formed in the elongate strap, wherein each of the plurality of pathways have an orientation that determines an orientation of a portion of the elongate strap threaded through one of the plurality of pathways with respect to a portion of the elongate strap forming the one of the plurality of pathways.

21. The posture support device according to claim 1, wherein the first split strap having two straps is disposed between the first end and the first pathway of the at least three pathways, and wherein the second split strap having two straps is disposed between the second pathway of the at least three pathways and a third pathway of the at least three pathways.

22. The posture support device according to claim 1, wherein the two straps of the first split strap having a first configuration where the two straps are parallel and a second configuration where the two straps are not parallel.

23. The posture support device according to claim 1, wherein the two straps of the second split strap having a first configuration where the two straps are parallel and a second configuration where the two straps are not parallel.

24. The posture support device according to claim 1, wherein, in a first configuration, the two straps of the first split strap are overlapping and have a thickness of the elongate strap and the two straps of the second split strap are overlapping and have a thickness of the elongate strap, and wherein, in a second configuration, the two straps of the first split strap are not overlapping and do not have the thickness of the elongate strap and the two straps of the second split strap are not overlapping and do not have the thickness of the elongate strap.

* * * * *